US007795011B2

(12) United States Patent
Park et al.

(10) Patent No.: US 7,795,011 B2
(45) Date of Patent: Sep. 14, 2010

(54) SAMPLE PROCESSING APPARATUS AND METHOD USING VACUUM CHAMBER

(75) Inventors: Tae-sik Park, Suwon-si (KR); Sung-hee Lee, Suwon-si (KR); Jung-ho Kang, Suwon-si (KR); Young-il Kim, Suwon-si (KR); Moon-chul Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1038 days.

(21) Appl. No.: 11/188,000

(22) Filed: Jul. 25, 2005

(65) Prior Publication Data

US 2006/0018801 A1 Jan. 26, 2006

(30) Foreign Application Priority Data

Jul. 24, 2004 (KR) ..................... 10-2004-0057898

(51) Int. Cl.
*C12M 1/34* (2006.01)
*C12M 3/00* (2006.01)
*C02F 9/00* (2006.01)

(52) U.S. Cl. ............. 435/288.5; 435/286.5; 435/286.6; 435/287.6; 435/288.3; 435/288.4; 435/305.2; 422/100; 422/102; 210/258; 210/406

(58) Field of Classification Search ............. 435/286.5, 435/286.6, 287.6, 288.3, 288.4, 288.5, 305.2; 422/100, 102; 210/258, 406
See application file for complete search history.

(56) References Cited

U.S. PATENT DOCUMENTS

| | | | | |
|---|---|---|---|---|
| 4,639,316 | A | 1/1987 | Eldegheidy | |
| 5,578,459 | A * | 11/1996 | Gordon et al. | 135/29 |
| 6,852,289 | B2 * | 2/2005 | Gordon et al. | 422/101 |
| 2002/0068357 | A1 | 6/2002 | Mathies et al. | |
| 2003/0109807 | A1 * | 6/2003 | Knoll | 600/583 |
| 2006/0166352 | A1 * | 7/2006 | Woudenberg et al. | 435/287.1 |
| 2007/0231851 | A1 * | 10/2007 | Toner et al. | 435/29 |
| 2009/0186403 | A1 * | 7/2009 | Tanaami et al. | 435/287.2 |

FOREIGN PATENT DOCUMENTS

| | | | |
|---|---|---|---|
| EP | 0 550 950 | A2 | 7/1993 |
| FR | 2 590 673 | A1 | 5/1987 |
| JP | 2002-277357 | A | 9/2002 |

* cited by examiner

*Primary Examiner*—William H Beisner
*Assistant Examiner*—Nathan A Bowers
(74) *Attorney, Agent, or Firm*—Sughrue Mion, PLLC

(57) ABSTRACT

A bio sample processing apparatus and method using vacuum chambers in which a bio sample is injected into a first vacuum chamber connected with one end of a bio processor and, after processing, is ejected into a second vacuum chamber connected with the other end of the bio processor. The vacuum chambers and bio processor are connected with each other to form an environment with a pressure lower than atmospheric pressure, and the bio sample moves toward the second vacuum chamber due to the pressure difference created by the injection of the bio sample into the first vacuum chamber.

13 Claims, 9 Drawing Sheets

SAMPLE PROCESSING APPARATUS AND METHOD USING VACUUM CHAMBER

CROSS-REFERENCE TO RELATED APPLICATIONS

This application claims the benefit under 35 U.S.C. §119 (a) from Korean Patent Application No. 2004-57898 filed on Jul. 24, 2004 in the Korean Intellectual Property Office, the disclosure of which is incorporated in its entirety herein by reference.

BACKGROUND OF THE INVENTION

1. Field of the Invention

Apparatuses consistent with the present invention relate generally to bio sample processing. More particularly, the present invention relates to a bio sample processing apparatus and method in which low-pressure vacuum chambers are set up in both ends of a bio processor and a bio sample is made to pass through the bio processor due to a pressure difference.

2. Description of the Related Art

A biochip is a biological micro chip that can analyze gene expression, the way of distribution, and mutation by arraying and immobilizing hundreds to hundreds of thousands of biomolecules such as deoxyribonucleic acid (DNA), DNA fragments, and ribonucleic acid (RNA), whose sequences are known, on a small solid substrate formed of glass, silicon, or nylon at predetermined intervals. As an example, biochip technology means DNA microarray technology which is up-to-date gene analysis technology. It may also mean a biosensor which combines bio substances with conventional physical, chemical and optical converters, a DNA microarray with a built-in DNA detector, a protein chip using proteins such as enzymes, antibodies and antigens, a cell chip using a vegetable cell, and a neuron chip directly using a neuron cell.

Recently, the concept of Lab-On-a-Chip (LOC) was introduced to the biochip technology field. LOC, DNA-LOC and protein-LOC are under development to integrate laboratory work, for example, sample pre-process, derivation, separation, and analysis, in one chip by directly using substantial bio samples such as blood, urine, cells, and saliva, and diverse kinds of samples such as natural substances, medicines, and food. LOC integrates valves, liquid measuring instruments, reactors, extractors, and separation systems as needed for sample pre-processing in an automatic analyzing device for analyzing a biochemical substance, integrating many sensor technologies in one chip.

In order to analyze a bio sample for substances contained in the bio sample by using a biochip, the bio sample should be pre-processed.

FIGS. 1A to 1C illustrate conventional pre-processing apparatuses for bio samples.

FIG. 1A shows an apparatus for separating a cell to be used as a bio sample. FIG. 1B shows a lysis apparatus for performing lysis on part of a cell to use it as a bio sample. FIG. 1C shows an apparatus for extracting molecules to be used as a bio sample from the part of a cell obtained in the lysis apparatus.

Referring to FIGS. 1A to 1C, pre-processing is performed to prepare a bio sample to be used in a biochip. The pre-processing of a bio sample includes cell separation, lysis, extraction, and purification for acquiring DNA and/or RNA to be used as the bio sample from cells.

FIGS. 2A to 2C illustrate conventional apparatuses for processing a bio sample.

FIG. 2A shows a general bio sample processing apparatus. FIG. 2B illustrates a LOC that can process and analyze a bio sample in one chip. FIG. 2C shows a conventional biosensor.

The conventional bio sample processing apparatus of FIG. 2A includes a macroscale external pump, a chamber, a valve, and a reactor. Since the bio sample processing apparatus does not have its own energy source, it uses an external pump to pre-process the bio sample. Because the bio sample processing apparatus is not for one time use, a cleaning process is necessary and it is hard to embody the bio sample processing apparatus to have multiple channels.

The LOC of FIG. 2B also needs an external energy source to process a bio sample, as in the case of FIG. 2A. Therefore, it includes a micro electromechanical (MEMS) pump inside, which makes the structure relatively complicated.

The conventional biosensor of FIG. 2C also does not have its own energy source, which is the same as the cases of FIGS. 2A and 2B. Therefore, the biosensor includes a micro pump inside, which is illustrated in FIG. 2C. When the micro pump is used, there are problems in that the process for fabricating the micro pump is quite complicated, and that the production cost is increased. In addition, the micro pump has relatively weak performance, compared to other pumps. Instead of forming the pump inside the biosensor, an external pump may be used. However, when an external pump is used, it is hard to connect and control the microstructure and the external pump.

SUMMARY OF THE INVENTION

It is, therefore, an exemplary aspect of the present invention to provide a bio sample processing apparatus using vacuum chambers that can process a bio sample without an external energy source by forming low-pressure vacuum chambers at both ends of a bio processor and making the bio sample pass through the bio processor due to a pressure difference between the chambers.

In accordance with an exemplary aspect of the present invention, there is provided an apparatus for processing a bio sample using vacuum chambers, which includes: a bio processor for pre-processing the bio sample to be analyzed; a first vacuum chamber having one open end and connected with one end of the bio processor, the first vacuum chamber into which the bio sample is injected; and a second vacuum chamber having one open end and connected with the other end of the bio processor. The bio sample is ejected into the second vacuum chamber after being processed through the bio processor. The open ends of the vacuum chambers and the bio processor are connected with each other to thereby form an environment with a pressure lower than atmospheric pressure, and the bio sample moves toward the second vacuum chamber due to a pressure difference between the first vacuum chamber and the second vacuum chamber that is caused by the injection of the bio sample.

The first and second vacuum chambers may be formed inside or outside the bio processor.

The bio sample processing apparatus may further comprise a diaphragm which is positioned between the first and second vacuum chambers and supports the bio processor, and a supporter for supporting the bio processor is formed inside the first vacuum chamber or inside the second vacuum chamber.

The bio sample processing apparatus may further comprise a valve which is formed outside the bio processor and provides a material required for the bio processing.

The bio sample is injected into the first vacuum chamber through the closed end of the first vacuum chamber by using a micro-sized needle, and the bio sample ejected into the second vacuum chamber can be acquired by using a micro-sized needle.

Consistent with another aspect of the present invention, there is provided a method for processing a bio sample in a bio sample processing apparatus provided with a bio processor for processing a bio sample and first and second vacuum chambers provided at both ends of the bio processor and having a pressure lower than atmospheric pressure, the method which includes the steps of: a) forming atmospheric pressure in the first vacuum chamber by injecting the bio sample into the first vacuum chamber; and b) moving the bio sample to the second vacuum chamber through the bio processor due to a pressure difference between the first vacuum chamber and the second vacuum chamber.

The vacuum chambers may be formed on both ends of the inside or outside of the bio processor, and the bio sample may be injected into the first vacuum chamber by using a micro-sized needle.

The method may further comprise a step of acquiring the bio sample moved to the second vacuum chamber by separating the second vacuum chamber from the bio processor. Also, the method may further comprise a step of acquiring the bio sample moved to the second vacuum chamber by using a micro-sized needle.

BRIEF DESCRIPTION OF THE DRAWINGS

The above aspects and features of the present invention will be more apparent by describing certain exemplary embodiments of the present invention with reference to the accompanying drawings, in which.

DETAILED DESCRIPTION OF EXEMPLARY, NON-LIMITING EMBODIMENTS OF THE INVENTION

Figure 1A:
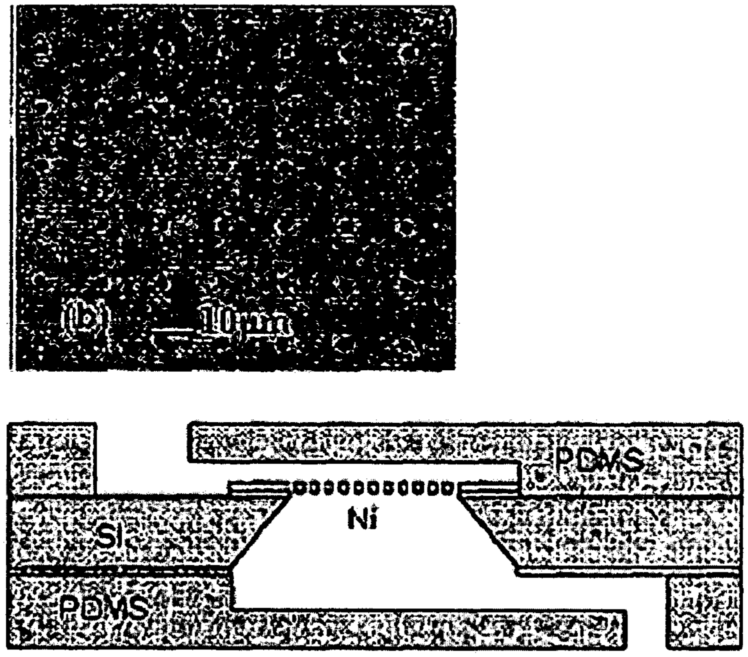
FIG. 1A (PRIOR ART)
FIGS. 1A to 1C illustrate conventional pre-processing apparatuses for bio samples.
Figure 1B:
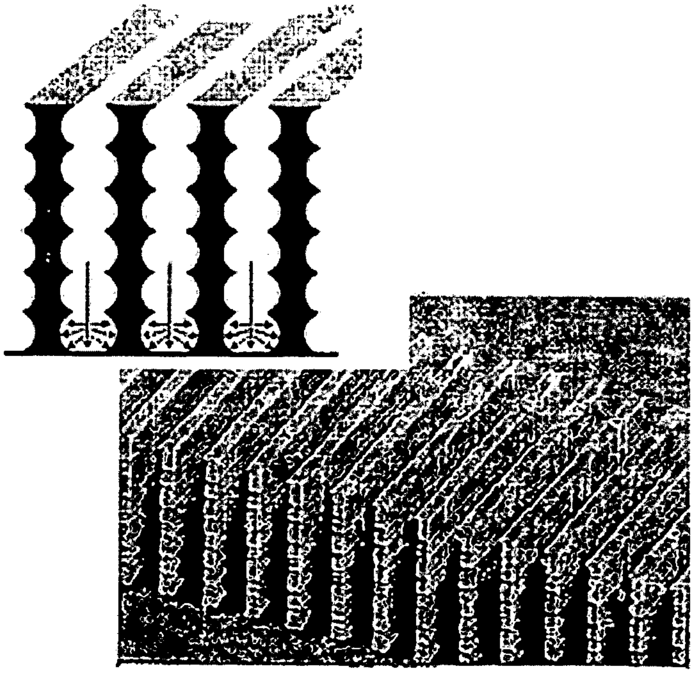
FIG. 1B (PRIOR ART)
Figure 1C:
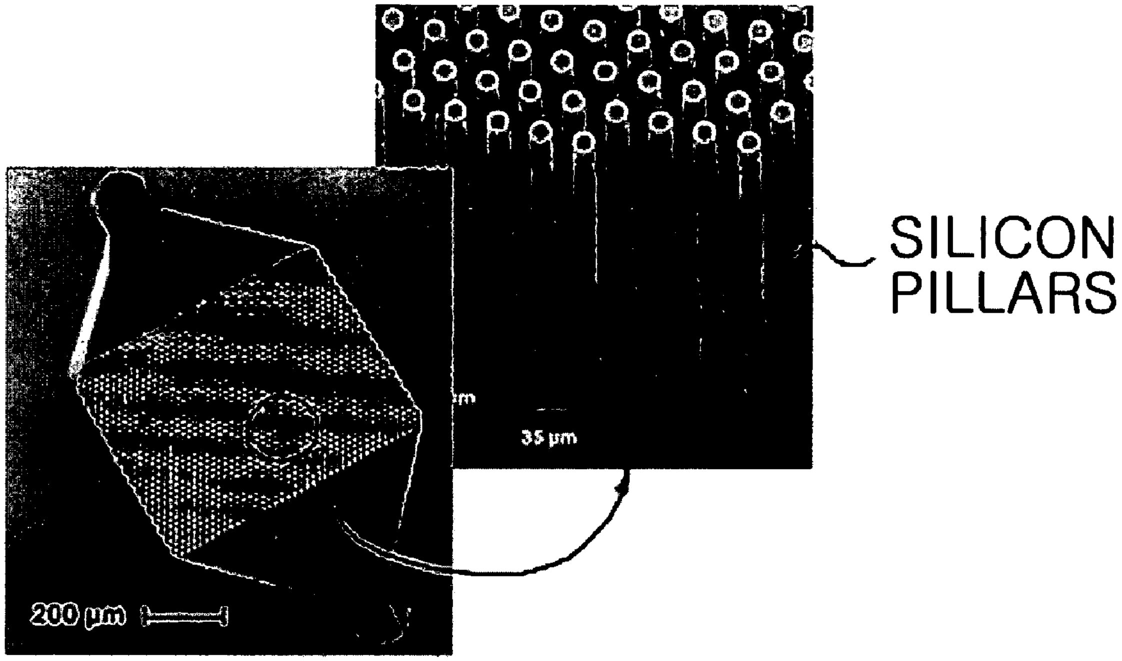
FIG. 1C (PRIOR ART)
Figure 2A:
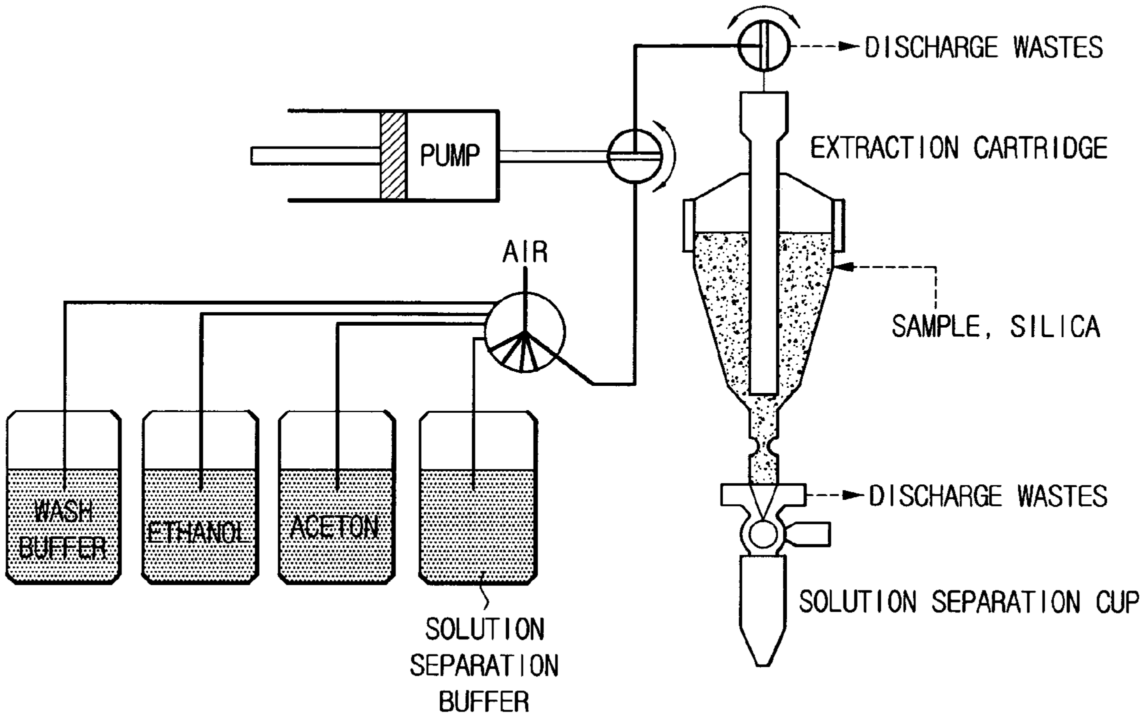
FIG. 2A (PRIOR ART)
FIGS. 2A to 2C illustrate conventional apparatuses for processing a bio sample.
Figure 2B:
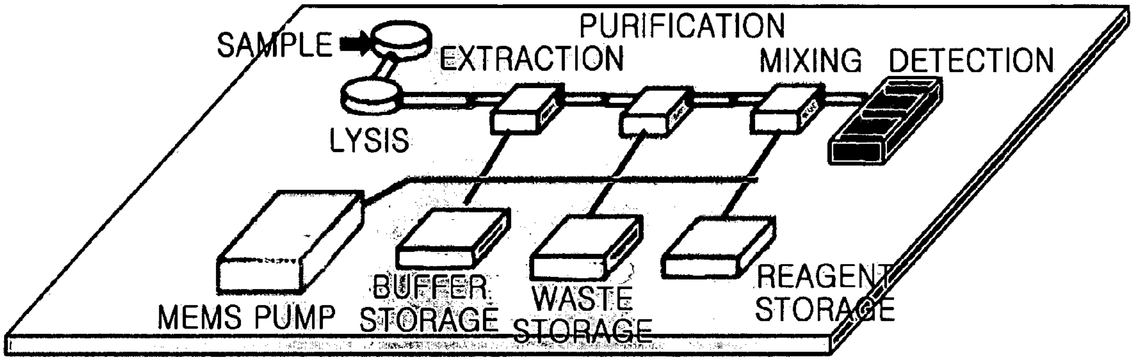
FIG. 2B (PRIOR ART)
Figure 2C:
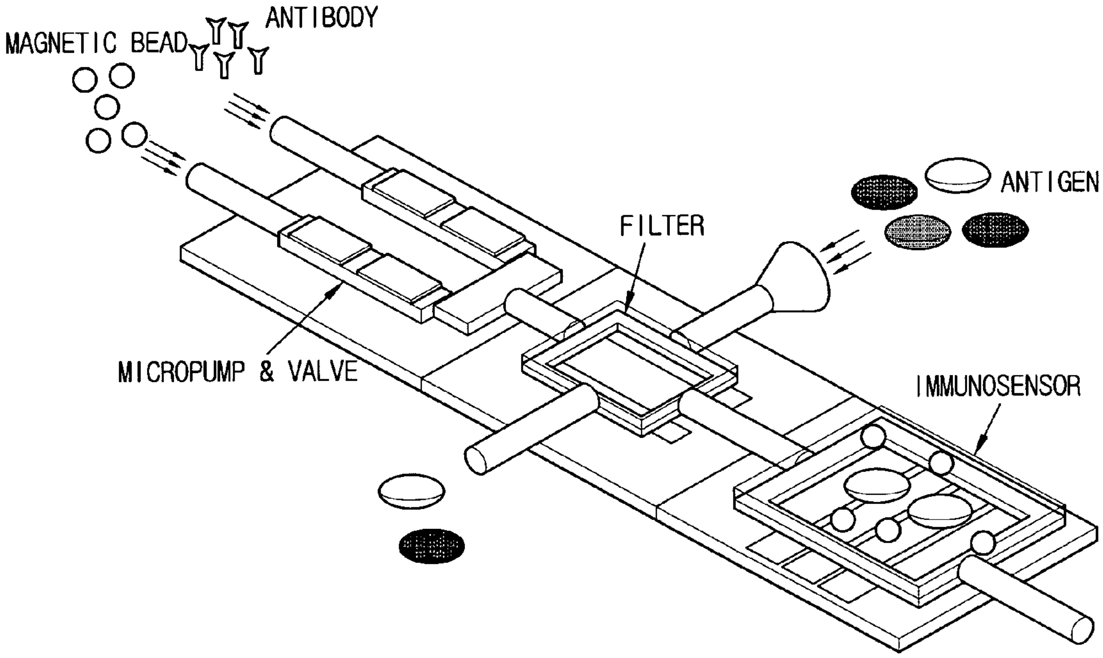
FIG. 2C (PRIOR ART)

Certain exemplary embodiments of the present invention will be described in greater detail with reference to the accompanying drawings.

In the following description, the same drawing reference numerals are used for the same elements even in different drawings. Matters described here, such as construction details and elements, are those which assist in a comprehensive understanding of the invention. It will be appreciated that the present invention can be carried out without describing well-known functions or constructions in detail.

Figure 3A:
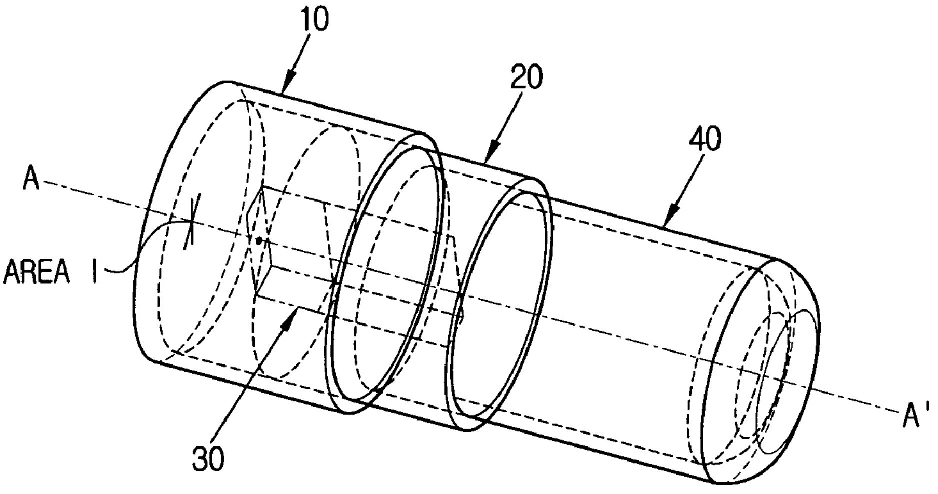
FIGS. 3A to 3D illustrate a bio sample processing apparatus using vacuum chambers consistent with a first exemplary embodiment of the present invention.
Figure 3B:
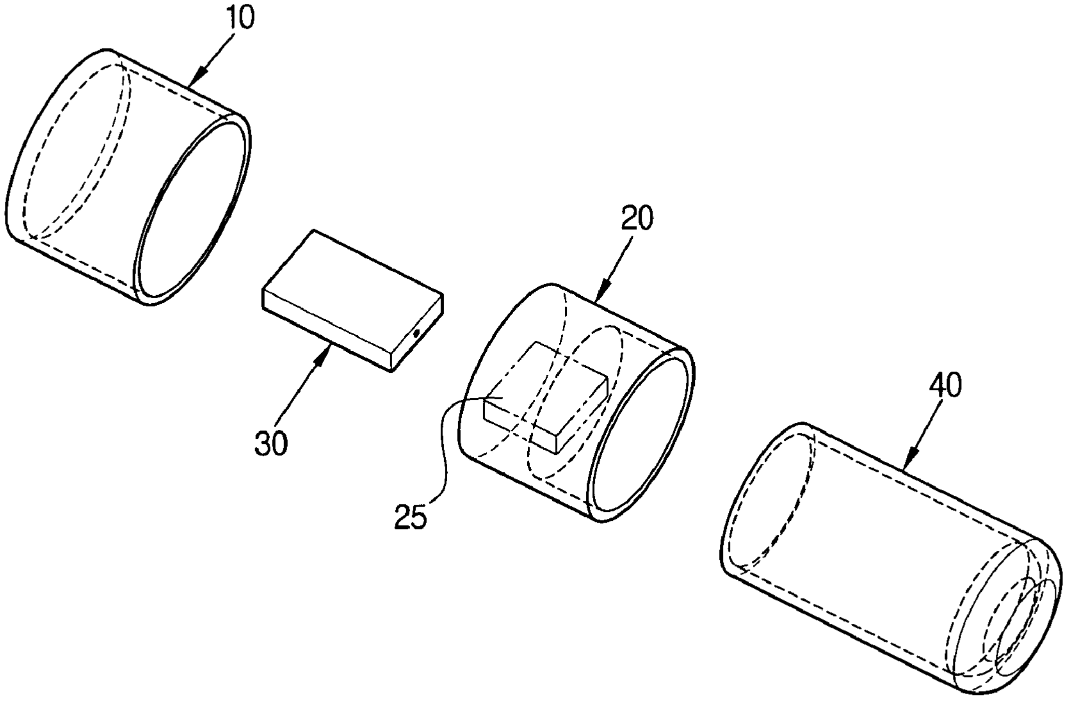
Figure 3C:
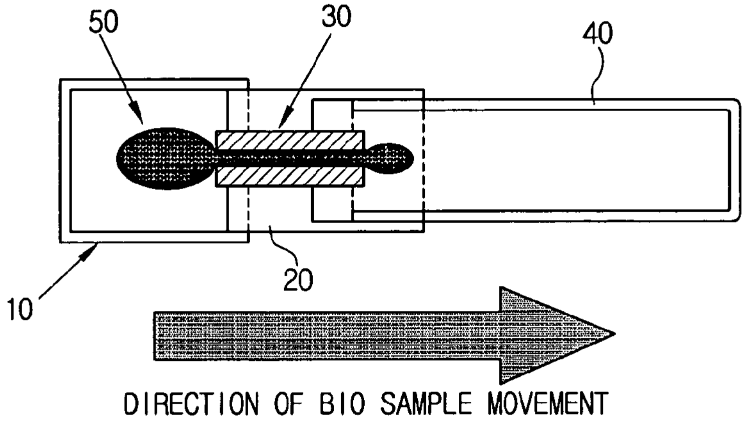
Figure 3D:
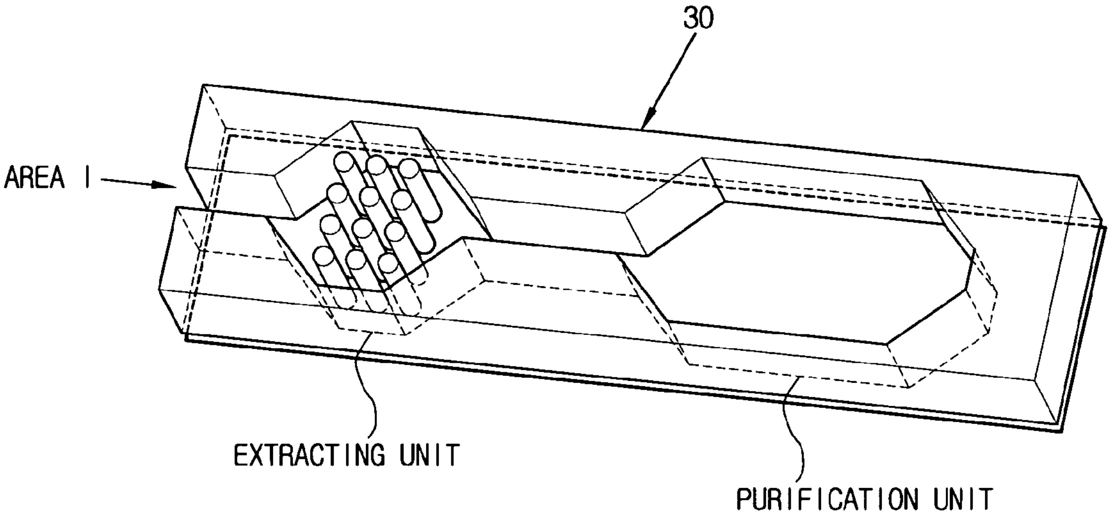

FIGS. 3A to 3D are diagrams of a bio sample processing apparatus using vacuum chambers consistent with an exemplary embodiment of the present invention. FIG. 3A is a perspective diagram showing the bio sample processing apparatus using vacuum chambers consistent with a first exemplary embodiment of the present invention. FIG. 3B is an exploded perspective diagram illustrating the bio sample processing apparatus of FIG. 3A. FIG. 3C is a cross-section view of the bio sample processing apparatus of FIG. 3A taken along section A-A'. FIG. 3D is a perspective interior view of an exemplary bio processor 30 of FIG. 3A.

With reference to FIGS. 3A through 3D, the bio sample processing apparatus includes a first vacuum chamber 10, a diaphragm 20, a supporter 25, a bio processor 30, and a second vacuum chamber 40.

The first vacuum chamber 10 has one open end and one closed end. The open end of the first vacuum chamber 10 is connected with the diaphragm 20. Due to the connection between the first vacuum chamber 10 and the diaphragm 20, a low pressure environment is formed inside the first vacuum chamber 10. Through the closed end of the first vacuum chamber 10, a bio sample 50 is injected with a micro-sized needle. The first vacuum chamber 10 is formed of a material which can be penetrated by the micro-sized needle easily. In FIG. 3A, area I is an area penetrated by the micro-sized needle.

The second vacuum chamber 40 also has one open end and one closed end. The open end of the second vacuum chamber 40 is connected with the diaphragm 20 to form a low pressure environment in the second vacuum chamber 40. In the second vacuum chamber 40, the bio sample 50 that has gone through bio processing such as filtering, lysis, extraction, and purification in the bio processor 30, is acquired. The acquired bio sample 50 can be obtained easily by separating the second vacuum chamber 40 from the diaphragm 20. The bio sample 50 can be obtained by using the micro-sized needle which is used for injecting the bio sample 50 into the first vacuum chamber 10.

The diaphragm 20 performs a role of supporting the bio processor 30 and includes a supporter 25 inside. The diaphragm 20 is connected with the open ends of the first and second vacuum chambers 10 and 40 to close the open ends and form low-pressure environment in the first and second vacuum chambers 10 and 40. The supporter 25 formed inside the diaphragm 20 has both ends open, and it is formed similar to the bio processor 30 so as to be connected with and support the bio processor 30. In FIGS. 3A and 3B, the supporter 25 is formed in the part of the diaphragm 20 where the diaphragm 20 is connected to the second vacuum chamber 40. However, the supporter 25 can be formed in the part of the diaphragm 20 where the diaphragm 20 is connected with the first vacuum chamber 10. Meanwhile, although the diaphragm 20 is connected with the first vacuum chamber 10 and the second vacuum chamber 40, individually, it can be formed to be integrated with any one of the first vacuum chamber 10 and the second vacuum chamber 40. In this case, the supporter 25 can be formed inside the first vacuum chamber 10 or the second vacuum chamber 40.

The bio processor 30 comprises, for example, a filtering unit, a lysis unit, a purification unit, and an extraction unit to process the bio sample 50, and has an opening in both ends. Through one of the openings, the bio sample 50 is injected. The injected bio sample 50 passes through the bio processor 30 and it is ejected out through the other opening.

The bio processor 30 is connected with the supporter 25 of the diaphragm 20 with both ends open and supported by the supporter 25. Since the diaphragm 20 is connected with the first vacuum chamber 10 and the second vacuum chamber 40, individually, the ends of the bio processor 30 come to be located inside the first and second vacuum chambers 10 and 40.

Figure 4A:
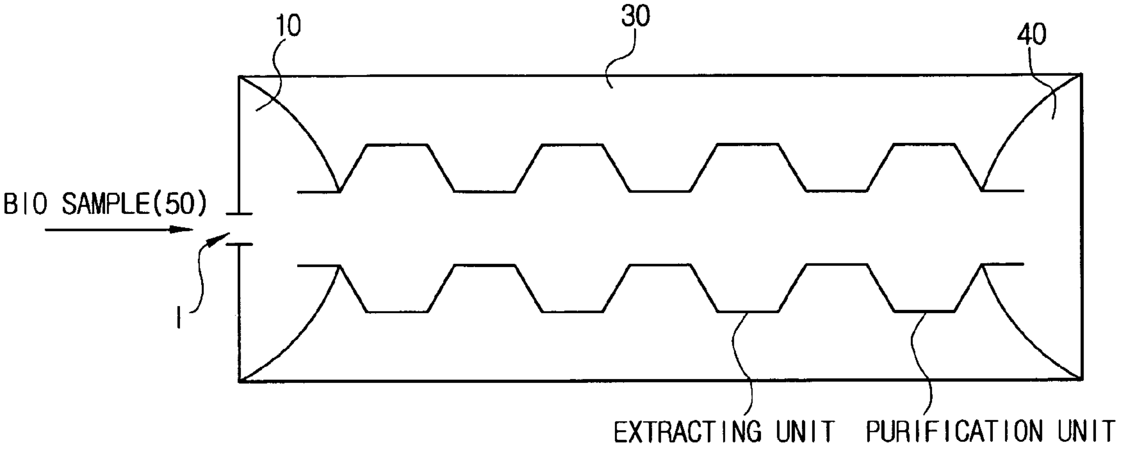
FIGS. 4A to 4B illustrate a bio sample processing apparatus using vacuum chambers consistent with a second exemplary embodiment of the present invention.
Figure 4B:
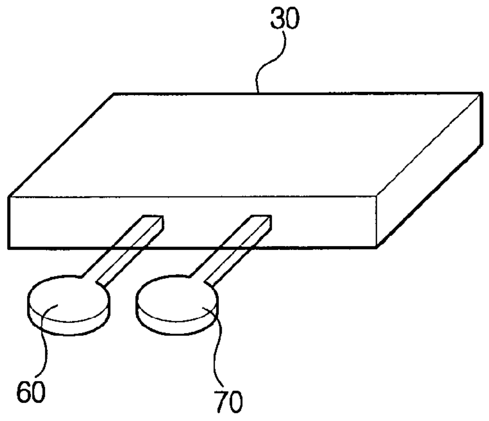

FIGS. 4A and 4B are diagrams of a bio sample processing apparatus using vacuum chambers consistent with a second exemplary embodiment of the present invention. FIGS. 3A to 3C show the vacuum chambers formed outside the bio processor 30. FIGS. 4A and 4B present a cross-sectional diagram and a perspective diagram of the vacuum chambers formed inside the bio processor 30, respectively. FIG. 4B also illustrates valves formed outside the bio processor 30.

Referring to FIG. 4A, the bio sample processing apparatus of the present invention includes a first vacuum chamber 10, a bio processor 30, and a second vacuum chamber 40. In contrast to the exemplary embodiment consistent with FIGS. 3A to 3D, the bio sample processing apparatus of FIG. 4A does not require a diaphragm 20 for supporting the bio processor 30, because the first and second vacuum chambers 10 and 40 are formed inside the bio processor 30. The first and second vacuum chambers 10 and 40 perform the same functions as described with reference to FIGS. 3A to 3D. In short, a low-pressure environment is formed inside the first and second vacuum chambers 10 and 40, and the bio sample 50 is injected into the first vacuum chamber 10 and, in the second vacuum chamber 40, the bio sample 50 that has passed through the bio processor 30 is acquired.

Referring to FIG. 4B, a first external valve 60 and a second external valve 70 are formed outside the bio processor 30. The first and second external valves 60 and 70 can be formed outside the bio processor 30, if necessary, and they may be used as a space for injecting solutions needed to process the bio sample 50 and/or a space for storing waste discharged from the processing.

Figure 5:
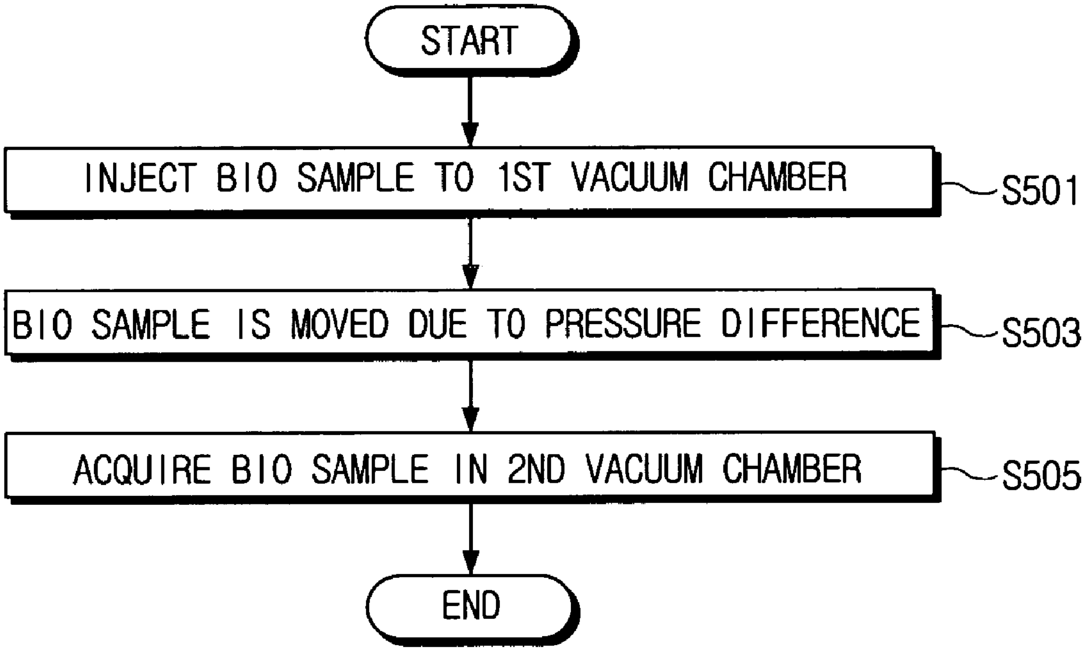
FIG. 5 is a flowchart describing a bio sample processing method using vacuum chambers consistent with an exemplary embodiment of the present invention.

FIG. 5 is a flowchart of a bio sample processing method using a vacuum chamber in accordance with an exemplary embodiment of the present invention.

Referring to FIG. 5, at step S501, the bio sample 50 is injected through a closed end of the first vacuum chamber 10. The bio sample 50 is injected into the area I of the first vacuum chamber 10, which is shown in FIG. 3A, by using a micro-sized needle. Therefore, the first vacuum chamber 10 is formed of a material that can be easily penetrated by the micro-sized needle.

Subsequently, at step S503, the bio sample 50 injected into the first vacuum chamber 10 moves toward the second vacuum chamber 40 through the bio processor 30. That is, the bio sample 50 moves in the arrow direction shown in FIG. 3C. As the bio sample 50 is injected into the first vacuum chamber 10, the pressure inside the first vacuum chamber 10, which is in the state of low pressure, becomes a state of atmospheric pressure. Therefore, the pressure inside the first vacuum chamber 10 becomes greater than the pressure inside the second vacuum chamber 40, and the pressure difference between the first vacuum chamber 10 and the second vacuum chamber 40 causes the bio sample 50 to traverse from the high-pressure first vacuum chamber 10 to the low-pressure second vacuum chamber 40. The bio sample 50, injected into the bio processor 30 through an opening formed on one side of the bio processor 30, goes through, for example, a series of filtering, lysis, extraction, and purification stages, and is ejected out of the bio processor 30 through an opening formed on the other side.

Subsequently, at step S505, the bio-processed bio sample 50 is acquired in the second vacuum chamber 40. The bio sample 50 acquired in the second vacuum chamber 40 can be obtained by using a micro-sized needle or a piston. If the first and second vacuum chambers 10 and 40 are formed outside the bio processor 30, the bio sample 50 can be obtained by separating the second vacuum chamber 40 from the diaphragm 20. If the first and second vacuum chambers 10 and 40 are formed inside the bio processor 30, the bio sample 50 can be obtained by cutting out the second vacuum chamber 40.

As described above, the present invention can provide an inexpensive bio sample processing apparatus having a simple structure, since no internal or external pump is used, by making the bio sample pass through the bio processor based on a pressure difference between the vacuum chambers set up in both ends of the bio processor.

Also, since the bio sample processing apparatus of the present invention does not require an external energy source for making the bio sample pass through the bio processor, bio samples can be processed conveniently regardless of time and place.

The foregoing embodiments and advantages are merely exemplary and are not to be construed as limiting the present invention. The present teaching can be readily applied to other types of apparatuses. Also, the descriptions of the exemplary embodiments of the present invention are intended to be illustrative, and not to limit the scope of the claims. Many alternatives, modifications, and variations will be apparent to those skilled in the art.

What is claimed is:

1. An apparatus for processing a bio sample, comprising:

a bio processor for processing a bio sample;

a first vacuum chamber having an open end and a closed end, wherein the open end is connected with an end of the bio processor, the bio sample being injected into the closed end of the first vacuum chamber;

a second vacuum chamber having an open end and a closed end, wherein the open end of the second vacuum chamber is connected with another end of the bio processor, the bio sample being processed through the bio processor before being ejected into the second vacuum chamber;

a diaphragm which is connected to the open ends of the first and second vacuum chambers so as to be disposed between the first and second vacuum chambers and which supports the bio processor; and valves which are formed outside the bio processor and are operable to provide a material required for the processing, wherein the first vacuum chamber, the second vacuum chamber, and the bio processor are connected with each other to form an environment with a pressure lower than atmospheric pressure before the bio sample is injected to the first vacuum chamber, and the injection of the bio sample into the closed end of the first vacuum chamber produces a Pressure within the first vacuum chamber that is larger than a pressure in the second vacuum chamber, thereby causing the bio sample to move from the first vacuum chamber toward the second vacuum chamber due to a pressure difference between the first vacuum chamber and the second vacuum chamber.

2. The apparatus as recited in claim 1, wherein the first and second vacuum chambers are formed inside the bio processor.

3. The apparatus as recited in claim 1, wherein a supporter for supporting and connecting with the bio processor is formed inside one of the first vacuum chamber and the second vacuum chamber.

4. The apparatus as recited in claim 1, wherein the closed end of the first vacuum chamber comprises a material through which a micro-sized needle can be inserted to inject the bio sample.

5. The apparatus as recited in claim 1, wherein the closed end of the second vacuum chamber comprises a material through which a micro-sized needle can be inserted to acquire the bio sample.

6. A method for processing a bio sample in a bio sample processing apparatus provided with a bio processor, first and second vacuum chambers having a pressure lower than atmospheric pressure, a diaphragm which is connected to the open ends of the first and second vacuum chambers, and valves formed outside the bio processor, the method comprising:

a) maintaining the atmospheric pressure before the bio sample is injected into the first vacuum chamber and then injecting the bio sample into a closed end of the first vacuum chamber to cause the pressure in the first vacuum chamber to become greater than the pressure in the second vacuum chamber; and b) moving the bio sample from an open end of the first vacuum chamber, through the bio processor, and into an open end of the second vacuum chamber based on a pressure difference between the first vacuum chamber and the second vacuum chamber without the use of a pump, wherein the valves are operable to provide a material required for the processing, and the diaphragm is disposed between the first and second vacuum chambers and supports the bio processor.

7. The method as recited in claim 6, wherein the first and second vacuum chambers are formed respectively at both ends of the inside or outside of the bio processor.

8. The method as recited in claim 6, further comprising injecting the bio sample into the first vacuum chamber by using a micro-sized needle.

9. The method as recited in claim 6, further comprising acquiring the bio sample moved to the second vacuum chamber by separating the second vacuum chamber from the bio processor.

10. The method as recited in claim 6, further comprising acquiring the bio sample moved to the second vacuum chamber by using a micro-sized needle.

11. The apparatus as recited in claim 1, wherein the first and second vacuum chambers are formed outside the bio processor.

12. An apparatus for processing a bio sample, comprising:

a bio processor for processing a bio sample;

a first vacuum chamber having an open end and a closed end, wherein the open end is connected with an end of the bio processor, the bio sample being injected into the closed end of the first vacuum chamber;

a second vacuum chamber having an open end and a closed end, wherein the open end of the second vacuum chamber is connected with another end of the bio processor, the bio sample being processed through the bio processor before being ejected into the second vacuum chamber;

a diaphragm which is connected to the open ends of the first and second vacuum chambers so as to be disposed between the first and second vacuum chambers and which supports the bio processor: and valves which are formed outside the bio processor and are operable to provide a material required for the processing, wherein the first vacuum chamber, the second vacuum chamber, and the bio processor are connected with each other to form an environment with a pressure lower than ambient pressure before the bio sample is injected to the first vacuum chamber, and the injection of the bio sample into the closed end of the first vacuum chamber produces a pressure within the first vacuum chamber that is larger than a pressure in the second vacuum chamber without using a pump, thereby causing the bio sample to move from the first vacuum chamber toward the second vacuum chamber due to a pressure difference between the first vacuum chamber and the second vacuum chamber.

13. A method for processing a bio sample in a bio sample processing apparatus provided with a bio processor, first and second vacuum chambers -having a pressure lower than ambient pressure, a diaphragm which is connected to the open ends of the first and second vacuum chambers, and valves formed outside the bio processor, the method comprising:

a) maintaining the ambient pressure before the bio sample is injected into the first vacuum chamber and then injecting the bio sample into a closed end of the first vacuum chamber to cause the pressure in the first vacuum chamber to become greater than the pressure in the second vacuum chamber; and b) moving the bio sample from an open end of the first vacuum chamber, through the bio processor, and into an open end of the second vacuum chamber based on a pressure difference between the first vacuum chamber and the second vacuum chamber without the use of a pump, wherein the valves are operable to provide a material required for the processing and, the diaphragm is disposed between the first and second vacuum chambers and supports the bio processor.

* * * * *